(12) United States Patent
Burwinkel et al.

(10) Patent No.: US 11,559,251 B2
(45) Date of Patent: Jan. 24, 2023

(54) SYSTEM AND METHOD FOR MANAGING PHARMACOLOGICAL THERAPEUTICS INCLUDING A HEALTH MONITORING DEVICE

(71) Applicant: Starkey Laboratories, Inc., Eden Prairie, MN (US)

(72) Inventors: Justin R. Burwinkel, Eden Prairie, MN (US); Peter J. Tetrick, Chaska, MN (US); Buye Xu, Sammamish, WA (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 59 days.

(21) Appl. No.: 16/802,113

(22) Filed: Feb. 26, 2020

(65) Prior Publication Data

US 2020/0268315 A1     Aug. 27, 2020

Related U.S. Application Data

(60) Provisional application No. 62/810,684, filed on Feb. 26, 2019.

(51) Int. Cl.
*A61B 5/00*     (2006.01)
*G16H 40/67*    (2018.01)
*G16H 20/10*    (2018.01)

(52) U.S. Cl.
CPC .......... *A61B 5/4848* (2013.01); *A61B 5/0022* (2013.01); *A61B 5/6815* (2013.01);
(Continued)

(58) Field of Classification Search
CPC ... A61B 5/6815; A61B 5/6816; A61B 5/0022; A61B 5/6803; A61B 5/4848
(Continued)

(56) References Cited

U.S. PATENT DOCUMENTS

| 6,650,871 B1 | 11/2003 | Cannon et al. |
| 9,167,356 B2 | 10/2015 | Higgins et al. |

(Continued)

FOREIGN PATENT DOCUMENTS

| JP | 2003511124 | 3/2003 |
| WO | 2020176632 | 9/2020 |

OTHER PUBLICATIONS

"International Search Report and Written Opinion," for PCT Application No. PCT/US2020/019917 dated May 8, 2020 (18 pages).
(Continued)

*Primary Examiner* — John R Downey
(74) *Attorney, Agent, or Firm* — Pauly, DeVries Smith & Deffner LLC

(57) ABSTRACT

Embodiments herein relate to systems, devices and methods for managing pharmacological therapeutics and aspects of the same. In an embodiment, a hearing assistance device can include a control circuit, an electroacoustic transducer for generating sound in electrical communication with the control circuit, a power supply circuit in electrical communication with the control circuit, and a sensor package in electrical communication with the control circuit. The control circuit can be configured to evaluate a signal from at least one of the sensors of the sensor package to detect administration of a therapy or receive data indicating that administration of a therapy has taken place. The control circuit can also be configured to record an instance of a detected medication administration event along with a timestamp. Other embodiments are also included herein.

16 Claims, 10 Drawing Sheets

(52) U.S. Cl.
CPC .......... *A61B 5/7405* (2013.01); *G16H 20/10* (2018.01); *G16H 40/67* (2018.01); *A61B 2560/0204* (2013.01); *A61B 2562/02* (2013.01)

(58) Field of Classification Search
USPC ................................................ 600/300, 301
See application file for complete search history.

(56) References Cited

U.S. PATENT DOCUMENTS

| | | | |
|---|---|---|---|
| 9,741,227 | B1 | 8/2017 | Kusens |
| 9,798,860 | B1 | 10/2017 | Movva |
| 9,981,107 | B2* | 5/2018 | Franceschetti ....... A61B 5/4266 |
| 2006/0064037 | A1* | 3/2006 | Shalon ................... G16H 20/60 600/586 |
| 2011/0199251 | A1* | 8/2011 | Iwata ..................... H01Q 1/247 342/27 |
| 2011/0276312 | A1* | 11/2011 | Shalon ................. A61B 5/6838 702/187 |
| 2013/0117696 | A1 | 5/2013 | Robertson et al. |
| 2014/0297006 | A1 | 10/2014 | Sadhu |
| 2015/0289820 | A1* | 10/2015 | Miller ................. A61B 5/4875 600/300 |
| 2016/0120453 | A1* | 5/2016 | Pop ..................... A61B 8/5223 600/437 |
| 2016/0342767 | A1 | 11/2016 | Narasimhan et al. |
| 2017/0006931 | A1* | 1/2017 | Guez ...................... A61B 5/369 |
| 2017/0032102 | A1 | 2/2017 | Skoda |
| 2017/0270820 | A1* | 9/2017 | Ashby .................. A61B 5/7465 |
| 2018/0000385 | A1 | 1/2018 | Heaton et al. |
| 2018/0132783 | A1* | 5/2018 | Wang ................. A61B 5/14546 |
| 2018/0184907 | A1 | 7/2018 | Tran |
| 2018/0220974 | A1 | 8/2018 | Schuman et al. |
| 2018/0228404 | A1 | 8/2018 | Bhunia et al. |
| 2018/0242859 | A1* | 8/2018 | Le ...................... A61B 5/14546 |
| 2019/0290129 | A1* | 9/2019 | Hanina .................. G16H 30/40 |
| 2020/0205746 | A1 | 7/2020 | Burwinkel et al. |
| 2020/0245869 | A1 | 8/2020 | Sivan et al. |
| 2020/0245938 | A1 | 8/2020 | Xu et al. |

OTHER PUBLICATIONS

Karani, Mamta V. et al., "The Role of Pharmacists in Preventing Falls among America's Older Adults," Front Public Health. 2016; 4: 250 (4 pages).

Paessler, Sebastian et al., "Food Intake Monitoring: an Acoustical Approach to Automated Food Intake Activity Detection and Classification of Consumed Food," Physiol. Meas. 33 (2012) 1073-1093 (21 pages).

"Sonos Boost Product Page," Sonos Inc, available as early as Sep. 4, 2016 via https://web.archive.org/web/20160904042146/https://www.sonos.com/en-us/shop/boost.html (5 pages).

* cited by examiner

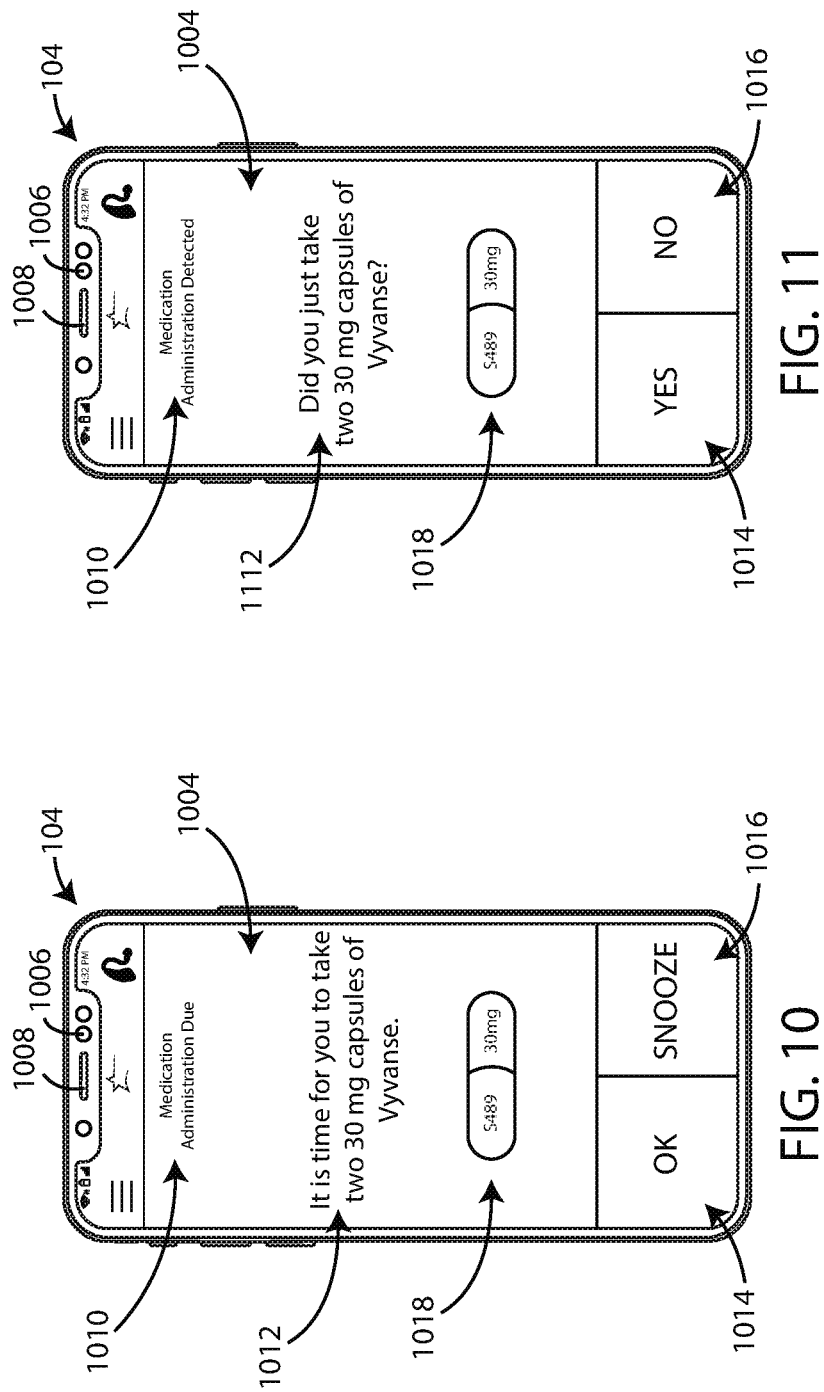

SYSTEM AND METHOD FOR MANAGING PHARMACOLOGICAL THERAPEUTICS INCLUDING A HEALTH MONITORING DEVICE

This application claims the benefit of U.S. Provisional Application No. 62/810,684, filed Feb. 26, 2019, the content of which is herein incorporated by reference in its entirety.

FIELD

Embodiments herein relate to systems, devices and methods for managing pharmacological therapeutics and aspects of the same.

BACKGROUND

Falls are the leading cause of both fatal and non-fatal injuries in people aged 65 years and older and can lead to significant costs, injuries, functional decline, and reduced quality of life. Some medications are known to result in adverse side-effects that may result in orthostatic hypotension, blurred vision, increased postural sway, unsteadiness, impaired alertness, and dizziness—all of which may contribute to falls. In many cases, a pharmacist can consult with the prescribing physician(s) and alternative medications may be prescribed to reduce the patient's medication-related falls risk.

More broadly, the Centers for Disease Control and Prevention (CDC) has identified pharmacists as a critical touchpoint for managing patients' outcomes. In fact, the CDC has recognized this fact and, consequently, developed the SAFE (i.e., Screen, Assess, Formulate, Educate) Medication Review Framework to assist pharmacists to conduct medication reviews with the aim of preventing older adult falls. Pharmacists also play a key role in monitoring how prescribed medications effect other relevant health conditions, such as heart rhythm, blood pressure, stress/mood, seizure, appetite, etc.

In addition, adherence to therapies is a primary determinant of treatment success. Failure to adhere to a treatment regimen can lead to substantial worsening of disease, death and increased health care costs. As such, pharmacists have a substantial interest in monitoring patient adherence to therapies and effects of the same.

SUMMARY

Embodiments herein relate to systems, devices and methods for managing pharmacological therapeutics and aspects of the same. In an embodiment, a hearing assistance device can include a control circuit, an electroacoustic transducer for generating sound in electrical communication with the control circuit, a power supply circuit in electrical communication with the control circuit, and a sensor package in electrical communication with the control circuit. The sensor package can include at least two of a motion sensor, a microphone, a heart rate sensor, a blood pressure sensor, a blood glucose sensor, a blood oximetry sensor, a temperature sensor, an electrocardiogram sensor, a galvanic skin response sensor, a cortisol level sensor, a neural activity sensor, and an eye movement sensor. The control circuit can be configured to evaluate a signal from at least one of the sensors of the sensor package to detect administration of a therapy or receive data indicating that administration of a therapy has taken place. The control circuit can be configured to record an instance of a detected medication administration event along with a timestamp.

In an embodiment, a health monitoring device is included having a control circuit, a motion sensor in electrical communication with the control circuit, a microphone in electrical communication with the control circuit, an electroacoustic transducer for generating sound in electrical communication with the control circuit, and a power supply circuit in electrical communication with the control circuit. The control circuit can be configured to evaluate a signal from at least one of the motion sensor and the microphone to detect a urination event and record the urination event along with a timestamp.

In an embodiment, a health monitoring device is included having a control circuit, a power supply circuit in electrical communication with the control circuit, and a sensor package in electrical communication with the control circuit. The sensor package can include at least two of a motion sensor, a microphone, a heart rate sensor, a blood pressure sensor, a blood glucose sensor, a blood oximetry sensor, a temperature sensor, an electrocardiogram sensor, a galvanic skin response sensor, a cortisol level sensor, a neural activity sensor, and an eye movement sensor. The control circuit can be configured to evaluate a signal from at least one of the sensors of the sensor package to detect administration of a therapy. The control circuit can be configured to record an instance of a detected medication administration event along with a timestamp.

In an embodiment, a method of operating a health monitoring device is included. The method can include placing the health monitoring device in the presence of a patient. The method can include processing the signal from at least one of the sensors of the sensor package to detect administration of a therapy to the patient. The method can also include recording an instance of a detected medication administration event along with a timestamp.

In an embodiment, a method of operating a health monitoring device is included. The method can include placing the health monitoring device in the presence of a patient. The method can include evaluating a signal from at least one of the motion sensor and the microphone to detect a urination event. The method can also include recording an instance of a detected urination event along with a timestamp.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 10 is a schematic view of an external visual display device and elements of a display screen thereof in accordance with various embodiments herein.

FIG. 11 is a schematic view of an external visual display device and elements of a display screen thereof in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, some medications are known to result in adverse side-effects and if a pharmacist knows of such side-effects occurring, then they can help such as by finding an alternative medication. By way of example, certain medications are known to increase fall risk and therefore pharmacists can play an important role in fall prevention by reviewing and optimizing medication therapy. Also, non-compliance with a therapeutic regimen can cause various problems, but if the pharmacist knows of the degree of compliance they can help to improve compliance.

However, patients are generally poor historians and their recounting of compliance with medical treatments may be poor. In addition, patients may fail to report or exaggerate negative side effects. Also, there can be a connection between compliance and side effect because medications are taken in few, large doses can cause more noticeable side-effects than if smaller, more frequent doses were administered throughout the day. Similarly, patients may not accurately report the occurrence of therapeutic effects of medication or other therapeutic regimens.

In accordance with various embodiments herein, a health monitoring device is included that can detect the occurrence or presence of side-effects and alert and/or inform a pharmacist or other patient care professionals regarding the same. In accordance with various embodiments herein, a health monitoring device is included that can detect the occurrence or presence of therapeutic effects and alert and/or inform a pharmacist or other patient care professionals regarding the same. In addition, in accordance with various embodiments herein, a health monitoring device is included that can detect compliance/non-compliance with a therapeutic regimen and alert and/or inform a pharmacist or other patient care professionals regarding the same. In various embodiments herein, systems and devices can remind the patient to take medications at a prescribed frequency that can allow their prescribing physician to utilize a smaller, more frequent dosing regimen that is less likely to result in side-effects while maximizing therapeutic efficacy. In accordance with various embodiments herein, a health monitoring device is included that can detect the occurrence or presence of medication administration events and signs of fall risk alert and/or inform a pharmacist or other patient care professionals regarding the same.

Figure 1:
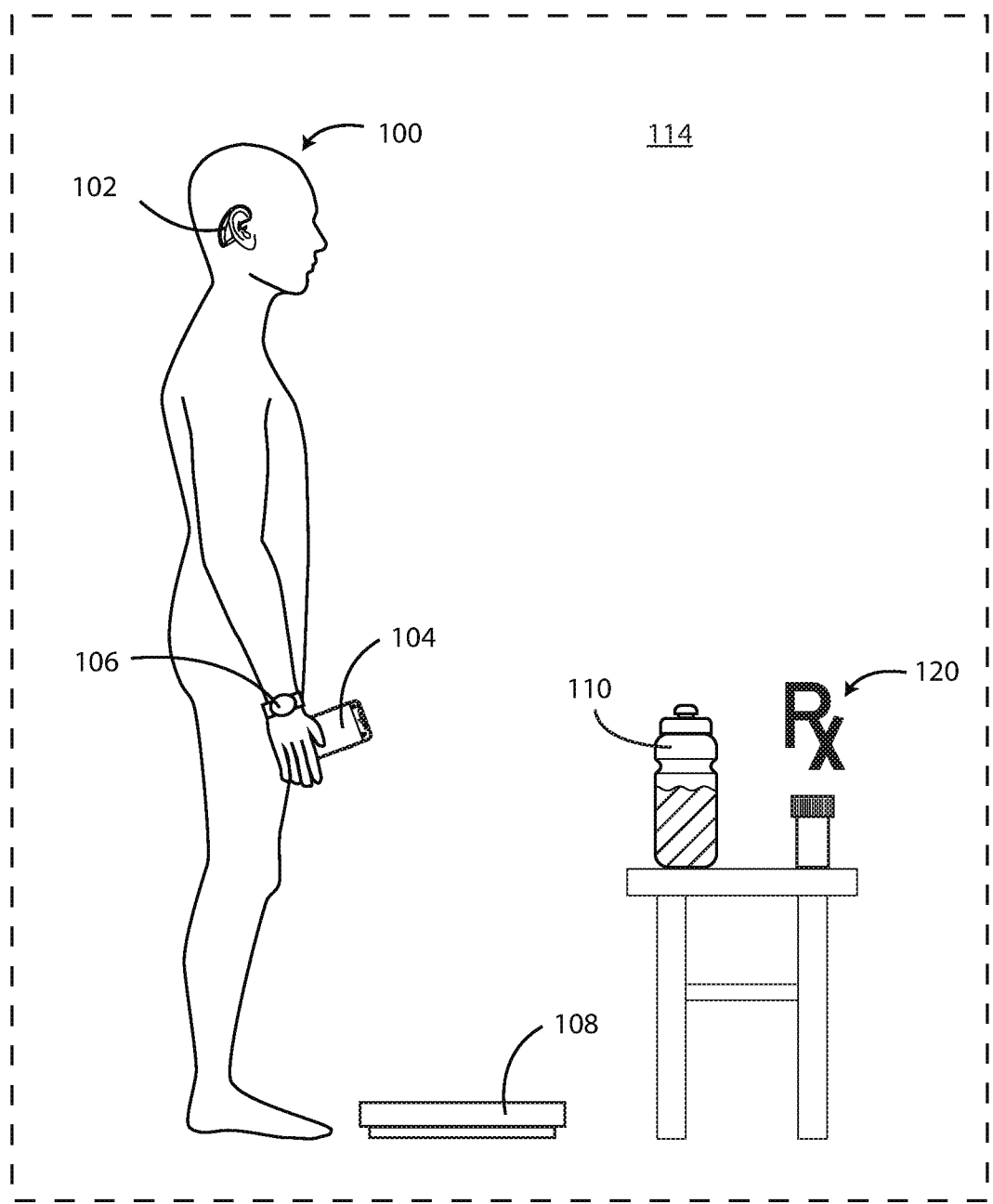
FIG. 1 is a schematic view of a patient in a remote environment with a health monitoring device in accordance with various embodiments herein.

Referring now to FIG. 1, a schematic view is shown of a patient 100 in a remote environment 114 with one or more health monitoring devices in accordance with various embodiments herein. The remote environment 114 can be "remote" such that it is in a location that is physically remote from a clinical care environment or a pharmacy. For example, the remote environment 114 could be the patient's home, place of work, or the like. However, in other scenarios, the patient 100 may be present in a care facility such as a clinic or a hospital.

The patient 100 may have one or more health monitoring devices, such as remote health monitoring devices. The health monitoring devices may take many different forms. In various embodiments, the health monitoring device can be a wearable health monitoring device. In some embodiments, the health monitoring device can be a hearing assistance device 102. In some embodiments, the health monitoring device can be a mobile or handheld computing device 104, such as a smart phone or the like. In some embodiments, the heath monitoring device can be wrist-worn device 106, such as a smart watch or the like. In some embodiments, the health monitoring device can be in communication (wired or wirelessly) with, a non-worn device including sensors and data transmission features such as weight scale 108, a water/liquid bottle 110, a pill container, a smart plate, a diet monitoring system, a basin, a sink, a toilet, or the like.

The health monitoring device(s) can be used to detect compliance/non-compliance with a therapeutic regimen such as the administration (self-administration or otherwise) of a prescription therapeutic 120. As will be shown, the health monitoring device(s) can alert and/or inform a pharmacist or other patient care professionals regarding the same. In various embodiments, the health monitoring device (s) can verify the administration of therapy by querying the patient (audibly, visually, audio visually, or the like).

In addition, the health monitoring device(s) can detect the occurrence or presence of side-effects (directly or indirectly). In various embodiments, the health monitoring device(s) can alert and/or inform a pharmacist or other patient care professionals regarding the same. In various embodiments, the health monitoring device(s) can remind or otherwise prompt the patient regarding the administration of therapy to improve compliance with a prescribed therapeutic regimen.

The health monitoring device can include a variety of sensors to gather data. Exemplary sensors are described in greater detail below. In some embodiments, data from sensors can be used to detect one or more physiological properties regarding the patient. In some embodiments, data from sensors can be used to gather information from or about the environment where the patient is to derive certain aspects about activities therein. In some embodiments, data from sensors can be used to detect medication administration events regarding the patient. In some embodiments, data from sensors can be used to detect properties, such as physiological properties, that are correlated to medication administration events. For example, changes in blood pressure or heart rate may be correlated to medication administration events and therefore data regarding those aspects can be used to derive data regarding medication administration events. In some embodiments, data from sensors can be used to detect the occurrence or presence of side effects, directly or indirectly. For example, if a potential side effect is syncope, in some cases data from sensors can be used to directly detect an occurrence of syncope. In other cases, if dizziness is a side effect, then this can be indirectly detected such as by detecting abnormal movement of the patient, e.g., swaying gait, seizure, nystagmus, etc. In some cases, therapeutic effects can be detected by observing a decrease in some occurrences.

Figure 2:
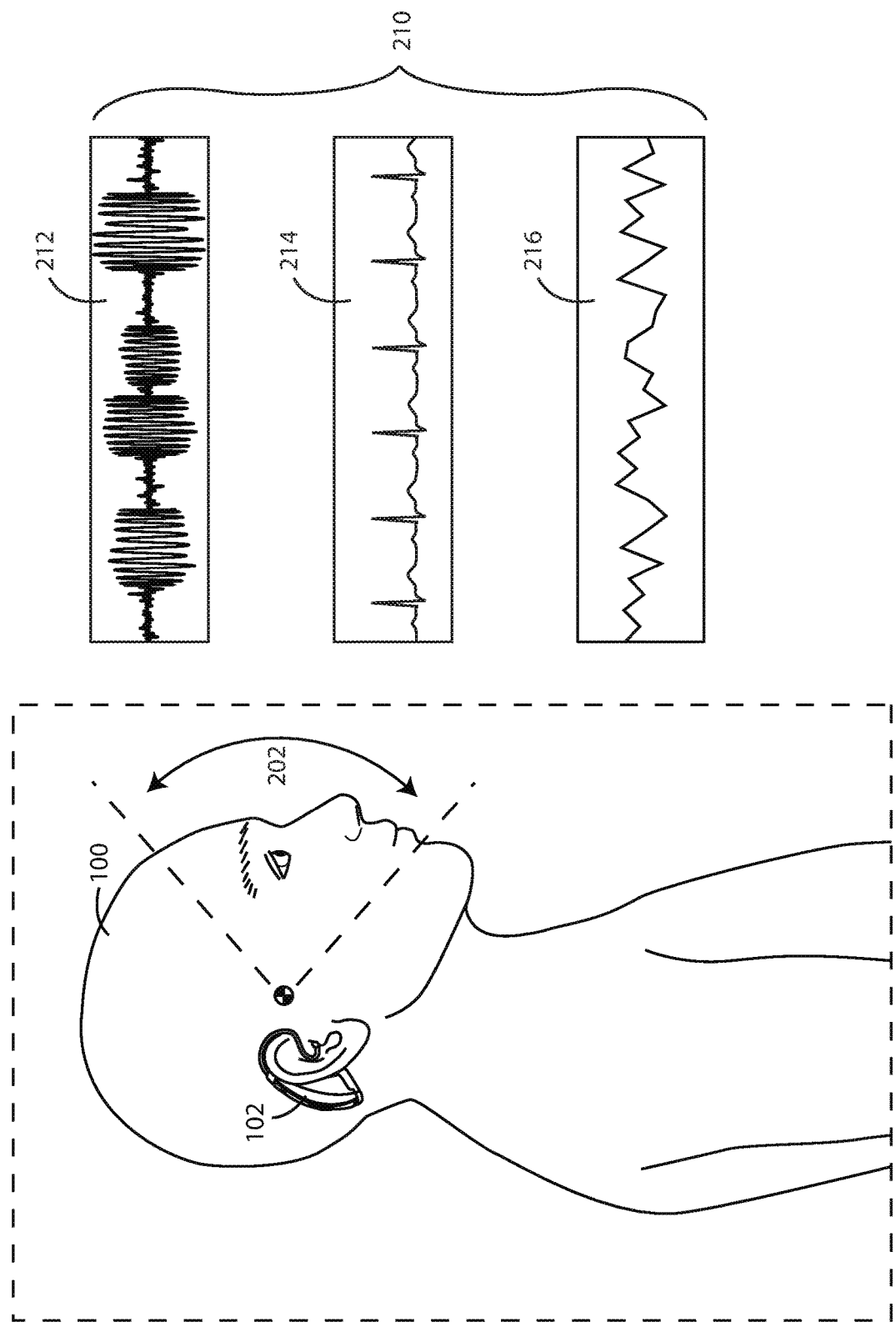
FIG. 2 is a schematic view of a patient wearing a health monitoring device and data gathered by the same in accordance with various embodiments herein.

Referring now to FIG. 2, a schematic view is shown of a patient 100 wearing a hearing assistance device 102 (which is merely one example of a health monitoring device) and data 210 gathered by the same in accordance with various embodiments herein. Many types of data 210 are contemplated herein. In some embodiments, the data 210 can include sound data 212. The sound data 212 can be gathered through a microphone or similar hardware component. In various embodiments, the hearing assistance device 102 can include a microphone or similar hardware component. The sound data 212 can relate directly to the patient 100, to actions the patient 100 is taking, and/or to the environment where the patient is.

In some embodiments, the data 210 can include physiological data 214. The physiological data 214 shown corresponds to heart rhythm data such as electrocardiogram data. However, it will be appreciated that physiological data 214 can include, but is not limited to, heart rhythm data, blood pressure data, heart rate data, blood glucose data, blood oximetry data, temperature data, galvanic skin response data, cortisol level data, neural activity data, eye movement data, and the like. In various embodiments, data 210 can also include other types of data 216 that varies over time. The data 216 can include data that is directly correlated to medication administration events. The data 216 can include data that is indirectly correlated to medication administration events.

The hearing assistance device 102 can also detect movement 202 of the patient and/or movement of a portion of the patient. For example, detected movement can include, but is not limited to, posture, head movement (rotation, side-to-side movement, vertical movement, etc.), arm movement, leg movement, torso position and movement, and the like.

In some embodiments, sensors can directly detect the administration of a therapeutic agent. In some embodiments, sensors can detect the administration of a therapeutic agent through detection of an event or pattern of something that is correlated with the administration of a therapeutic agent.

Figure 3:
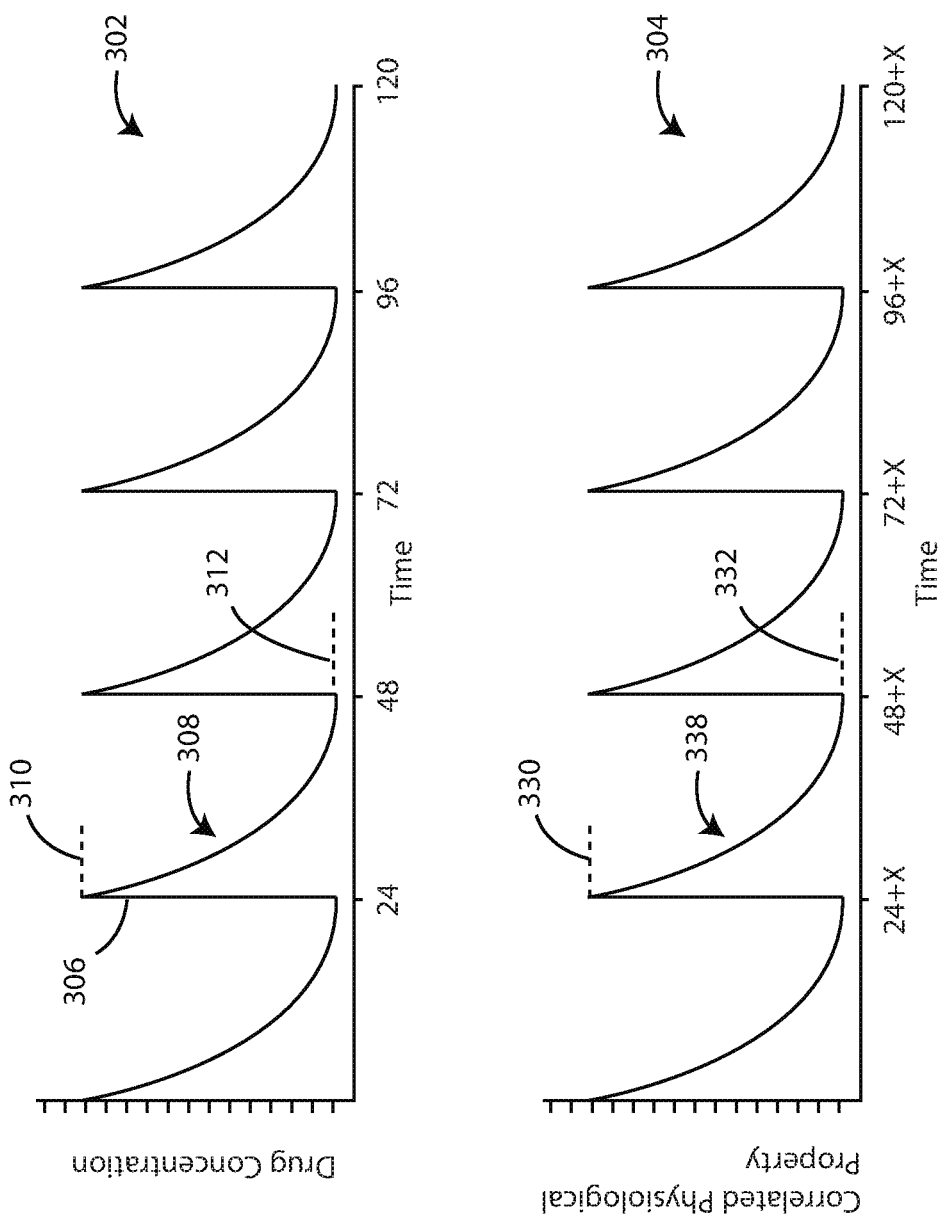
FIG. 3 is a schematic view of drug concentration in the blood of a patient over time in comparison with an index of a correlated physiological property over time in accordance with various embodiments herein.

Referring now to FIG. 3, a schematic view is shown of drug concentration in the blood of a patient over time in comparison with an index of a correlated physiological property over time in accordance with various embodiments herein. In this hypothetical example, the drug concentration is shown assuming administration every 24 hours of a medication having a physiological half-life of 6 hours. As such, the idealized graph 302 of drug concentration (serum or blood concentration) over time includes administration events 306 occurring every 24 hours whereupon drug concentration reaches a maximum value 310 followed by exponential decay 308 over the following 24 hours down to a minimum value 312 before the next administration event.

A measurable property (such as a physiological property) can be correlated with drug concentration. As such, the idealized graph 304 of the measurable property includes a maximum value 330 followed by exponential decay 338 over the following 24 hours down to a minimum value 332 before the next administration event. By measuring peaks of a correlated measurable property, the number of medication administration events can be derived. In some embodiments, various signal processing operations can be performed on signals relating to correlated measurable properties including frequency filtering (high pass, low pass, band pass), threshold value filtering, time shifting (e.g., time offset), time scaling, time reversal, amplitude scaling, addition of signals, multiplication of signals, differentiation of signals, integration of signals, and the like.

In some cases, the correlation can include a time offset "X". Time offset "X" can depend on the particular therapeutic agent. In some embodiments, the time offset ("X") can be greater than or equal to 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, or 150 minutes. In some embodiments, the time offset ("X") can be less than or equal to 300, 295, 290, 285, 280, 275, 270, 265, 260, 255, 250, 245, 240, 235, 230, 225, 220, 215, 210, 205, 200, 195, 190, 185, 180, 175, 170, 165, 160, 155, or 150 minutes. In some embodiments, the time offset ("X") can fall within a range of 0 to 300 minutes, or 5 to 295 minutes, or 10 to 290 minutes, or 15 to 285 minutes, or 20 to 280 minutes, or 25 to 275 minutes, or 30 to 270 minutes, or 35 to 265 minutes, or 40 to 260 minutes, or 45 to 255 minutes, or 50 to 250 minutes, or 55 to 245 minutes, or 60 to 240 minutes, or 65 to 235 minutes, or 70 to 230 minutes, or 75 to 225 minutes, or 80 to 220 minutes, or 85 to 215 minutes, or 90 to 210 minutes, or 95 to 205 minutes, or 100 to 200 minutes, or 105 to 195 minutes, or 110 to 190 minutes, or 115 to 185 minutes, or 120 to 180 minutes, or 125 to 175 minutes, or 130 to 170 minutes, or 135 to 165 minutes, or 140 to 160 minutes, or 145 to 155 minutes, or can be about 150 minutes.

In some cases, the correlated physiological property can be directly measured. In other cases, the correlated physiological property can be indirectly measured.

Certain medications are known to increase fall risk. In accordance with various embodiments herein, a health monitoring device is included that can detect the occurrence or presence of medication administration events and signs of fall risk. According to some embodiments, a health monitoring device may alert and/or inform a pharmacist or other patient care professionals regarding the same. In some embodiments, a health monitoring device can provide alerts based upon a predicted fall risk value. Aspects of calculating fall risk values are described in U.S. Prov. Pat. App. No. 62/785,295, titled "Predictive Fall Event Management System and Method of Using", the content of which is herein incorporated by reference.

Figure 4:
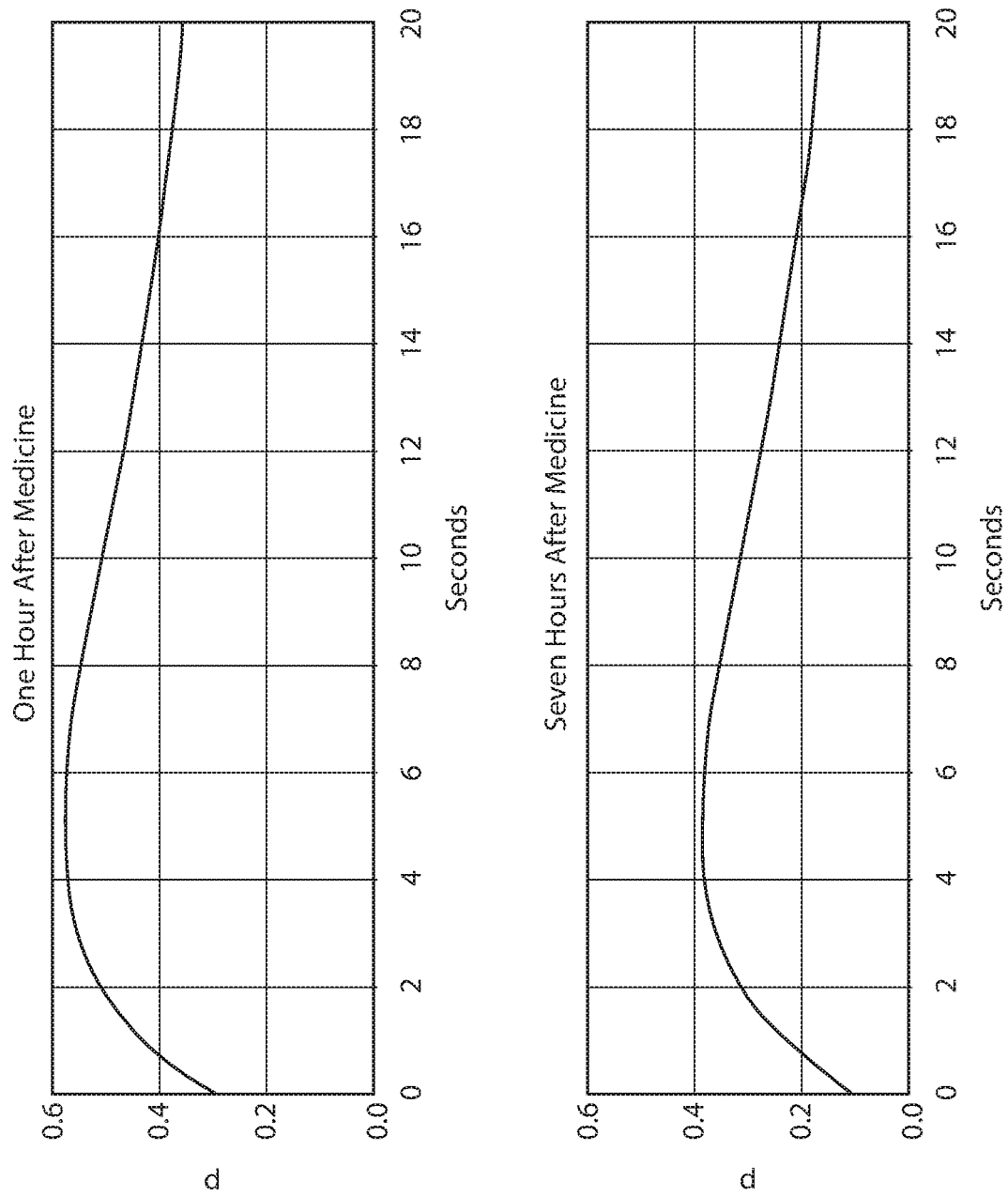
FIG. 4 is an idealized view of patient fall risk over time as a function of how recently a medication was taken.

Referring now to FIG. 4, an idealized view is shown of patient fall risk over time as a function of how recently a medication was taken. In the graph labeled "One Hour After Medicine" the risk of falling "p" is shown over a period of second corresponding to a patient getting up out of a chair. By four seconds after the patient beginning to get up, the risk of falling has risen to almost 0.6. In the graph labeled "Seven Hours After Medicine" the risk of falling similarly rises substantially as the patient begins to get up. However, by four seconds after the patient beginning to get up, the risk of falling has risen to only close to 0.4, not 0.6. As such, a comparison of these two idealized graphs shows the increase in risk of falling resulting from administration of this particular medication. As such, tracking medication administration events can provide insight to a pharmacist or other care professional regarding fall risks faced by patients.

Figure 5:
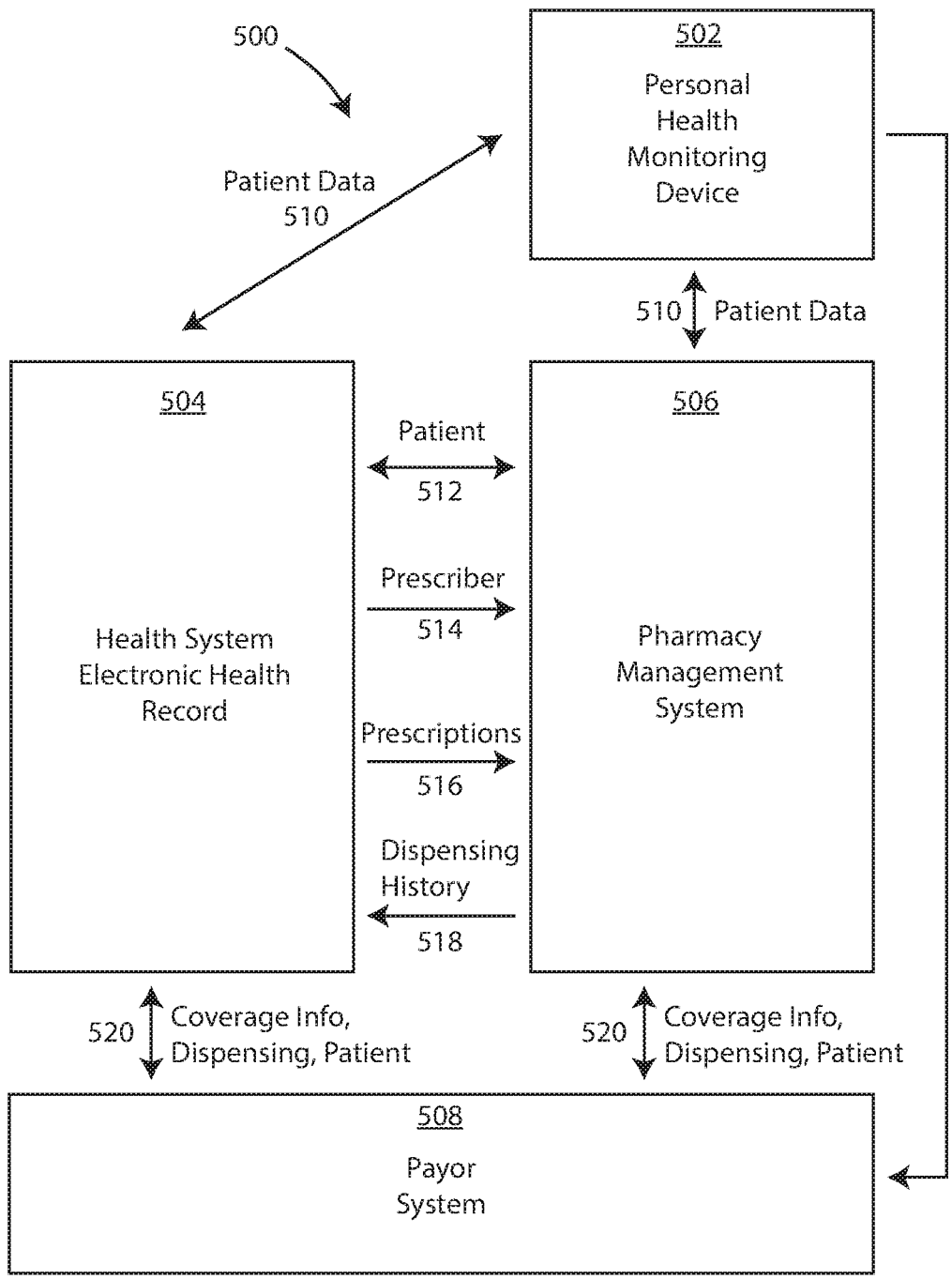
FIG. 5 is a schematic view of components of a system for managing pharmacological therapeutics in accordance with various embodiments herein.

Systems for managing pharmacological therapeutics can include many different components. Referring now to FIG. 5, a schematic view is shown of components of a system 500 for managing pharmacological therapeutics in accordance with various embodiments herein.

A personal health monitoring device 502 can provide information of the types described elsewhere herein (broadly categorized as "patient data" 510) to a pharmacy management system 506. Exemplary pharmacy management systems can include, but are not limited to, Intercom Plus, RxConnect, NexGen, AbacusRx, Liberty Software, Pioneer Rx, and the like. The pharmacy management system 506 can interface with a health provider (or health system) electronic health record system 504. Patient data 512 can be exchanged between the pharmacy management system 506 and the health provider electronic health record system 504. Prescriber data 514 and prescription information 516 can be passed from the health provider electronic health record system 504 to the pharmacy management system 506. Dispensing information 518 (including, but not limited to, dispensing history) can be pass from the pharmacy management system 506 to the health provider electronic health record system 504. Various pieces of data 520 can be exchanged between the pharmacy management system 506 and the payor system 508 including, but not limited to, coverage information, formulary information, dispensing information, patient information, etc. Similarly, various piece of data 520 can be exchanged between the health system (or health provider) electronic health record system 504 and the payor system 508. It should be appreciated that any suitable data security and authentication methods may be utilized to protect patient privacy as data is shared between a personal health monitoring device, a pharmacy management system, an electronic health record system, a payor system, and the like. In some embodiments, the personal health monitoring device 502 can alert the pharmacy management system that the patient is displaying adverse interactions or is at risk for falling.

In some embodiments, a user (patient, care provider, etc.) can manually input prescription data for reminders or to track responses to the medications themselves, or to share with others, without needing a fully integrated electronic medical record system. As such, in some embodiments, a system herein can receive inputs from a patient or a third party (such as a care provider) pertaining to prescription data and store the same.

Figure 6:
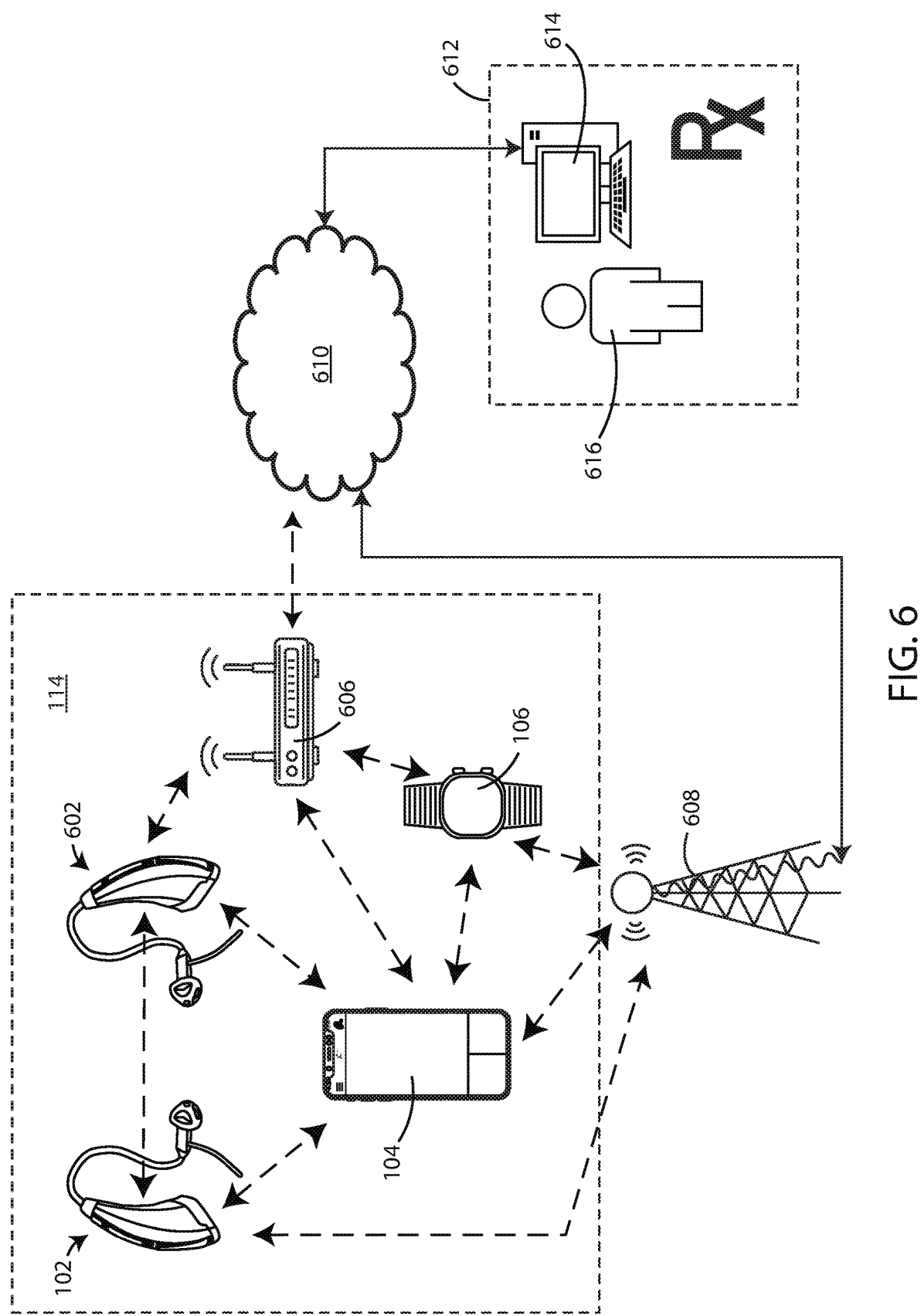
FIG. 6 is a schematic view of components of a system for managing pharmacological therapeutics in accordance with various embodiments herein.

It will be appreciated that data and/or signals can be exchanged between many different components in accordance with embodiments herein. Referring now to FIG. 6, a schematic view is shown of data and/or signal flow as part of a system in accordance with various embodiments herein. In the remote location/environment 114, a patient (not shown) can have a first hearing assistance device 102 and a second hearing assistance device 602. Each of the hearing assistance devices 102, 602 can include sensor packages as described herein including, for example, an IMU. The hearing assistance devices 102, 602 and sensors therein can be disposed on opposing lateral sides of the patient's head. The hearing assistance devices 102, 602 and sensors therein can be disposed in a fixed position relative to the patient's head. The hearing assistance devices 102, 602 and sensors therein can be disposed within opposing ear canals of the patient. The hearing assistance devices 102, 602 and sensors therein can be disposed on or in opposing ears of the patient. The hearing assistance devices 102, 602 and sensors therein can be spaced apart from one another by a distance of at least 3, 4, 5, 6, 8, 10, 12, 14, or 16 centimeters and less than 40, 30, 28, 26, 24, 22, 20 or 18 centimeters, or by a distance falling within a range between any of the foregoing.

While FIG. 6 shows a patient with two hearing assistance devices, it will be appreciated that in various scenarios the patient will only have a single hearing assistance device. However, while not intending to be bound by theory, there can be various advantages to the use of two hearing assistance device. By way of example, detection of events and communications regarding the same can be more robust. Detection of events can be more robust because data from one device can be verified against data from the other device. In addition, based on location associated with opposing ears, some aspects may be more readily sensed from one side of the head or another in a given situation. Data communications can also be more robust as both devices can communicate with an external device, such as a handheld computing device or the like. As another example, power management can be more efficient by implementing a duty cycling approach that alternately uses sensors from one device or the other.

In various embodiments, data and/or signals can be exchanged directly between the first hearing assistance device 102 and the second hearing assistance device 602. A handheld computing device 104 with a video display screen, such as a smart phone, can also be disposed within the remote location/environment 114.

The handheld computing device 104 can exchange data and/or signals with one or both of the first hearing assistance device 102 and the second hearing assistance device 602 and/or with an accessory to the hearing assistance devices (e.g., a remote microphone, a remote control, a phone streamer, etc.). The handheld computing device 104 can also exchange data across a data network to the cloud 610, such as through a wireless signal connecting with a local gateway device, such as a network router 606 or through a wireless signal connecting with a cell tower 608 or similar communications tower. In some embodiments, the handheld computing device can also connect to a data network to provide communication to the cloud 610 through a direct wired connection.

In some embodiments, a device other than a handheld computing device can exchange data and/or signals with one or both of the first hearing assistance device 102 and the second hearing assistance device 602 and/or with an accessory to the hearing assistance devices (e.g., a remote microphone, a remote control, a phone streamer, etc.) and exchange data across a data network to the cloud 610. For example, a device such as a smart-home device (e.g., Amazon Echo, Google Home, etc.) can exchange data and/or signals with one or both of the first hearing assistance device 102 and the second hearing assistance device 602 and/or with an accessory to the hearing assistance devices (e.g., a remote microphone, a remote control, a phone streamer, etc.) and exchange data across a data network to the cloud 610.

In some embodiments, a care provider 616 (such as an audiologist, physical therapist, a physician or a different type of clinician, specialist, or care provider, or physical trainer) can receive information from devices at the remote location/environment 114 remotely at a second location 612 through a data communication network such as that represented by the cloud 610. The care provider 616 can use a computing device 614 to access and interact with the information received. The received information can include, but is not limited to, information regarding the patient's compliance with the prescribed therapeutic regimen, the occurrence of side effects, the occurrence of therapeutic effects, spatial position information related to IMU and/or accelerometer data, trends related to any of these and the like. In some embodiments, received information can be provided to the care provider 616 in real time. In some embodiments, received information can be stored and provided to the care provider 616 at designated time points.

In some embodiments, the care provider 616 (such as a pharmacist, a physician or a different type of clinician, specialist, or care provider) can send information remotely from the second location 612 through a data communication network such as that represented by the cloud 610 to devices at the remote location/environment 114. For example, the care provider 616 can enter information into the computing device 614, can use a camera connected to the computing device 614 and/or can speak into the computing device. The sent information can include, but is not limited to, feedback information, queries on side effects, encouragement regarding medication administration, nutrition and hydration recommendations, other health and wellness guidance information, and the like. In some embodiments, information from the care provider 616 can be provided to the patient in real time.

Heath monitoring devices, including hearing assistance devices (hearing aids and hearables (e.g., wearable earphones)), can include an enclosure, such as a housing or shell, within which internal components are disposed. Components of a hearing assistance device herein can include a control circuit, digital signal processor (DSP), memory (such as non-volatile memory), power management circuitry, a data communications bus, one or more communication devices (e.g., a radio, a near-field magnetic induction device), one or more antennas, one or more microphones, a receiver/speaker, and various sensors as described in greater detail below. More advanced hearing assistance devices can incorporate a long-range communication device, such as a BLUETOOTH® transceiver or other type of radio frequency (RF) transceiver.

Figure 7:
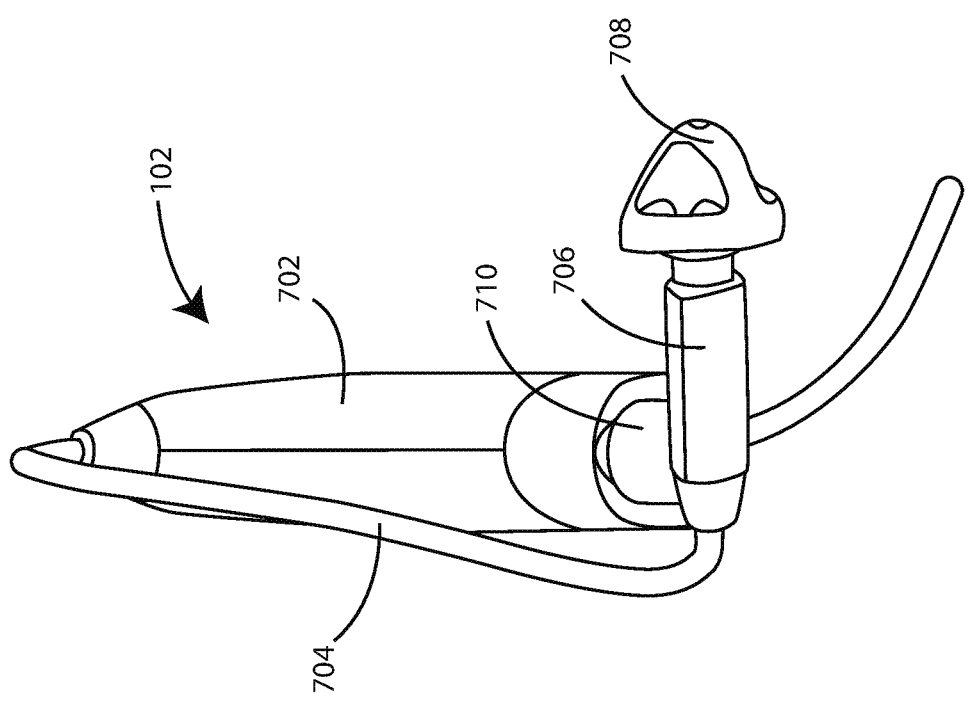
FIG. 7 is a schematic view of a hearing assistance device in accordance with various embodiments herein.

Health monitoring devices herein may take many different forms. In various embodiments, the health monitoring device can be a wearable health monitoring device. In some embodiments, the health monitoring device can be a hearing assistance device. In some embodiments, the hearing assistance device can be a hearing aid falling under 21 C.F.R. § 801.420. Referring now to FIG. 7, a schematic view of a hearing assistance device 102 is shown in accordance with various embodiments herein. The hearing assistance device 102 can include a hearing device housing 702. The hearing device housing 702 can define a battery compartment 710 into which a battery can be disposed to provide power to the device. The hearing assistance device 102 can also include a receiver 706 adjacent to an earbud 708. The receiver 706 can include a component that converts electrical impulses into sound, such as an electroacoustic transducer, speaker, or loud speaker. A cable 704 or connecting wire can include one or more electrical conductors and provide electrical communication between components inside of the hearing device housing 702 and components inside of the receiver 706.

The hearing assistance device 102 shown in FIG. 7 is a receiver-in-canal type device and thus the receiver is designed to be placed within the ear canal. However, it will be appreciated that many different form factors for hearing assistance devices are contemplated herein. As such, hearing assistance devices herein can include, but are not limited to, behind-the-ear (BTE), in-the ear (ITE), in-the-canal (ITC), invisible-in-canal (IIC), receiver-in-canal (RIC), receiver in-the-ear (RITE) and completely-in-the-canal (CIC) type hearing assistance devices.

In another example, hearing assistance device(s) 102 can include one or more Personal Sound Amplification Products (PSAPs). In another example, hearing assistance device(s) 102 can include one or more cochlear implants, cochlear implant magnets, cochlear implant transducers, and cochlear implant processors. In another example, hearing assistance device(s) 102 can include one or more "hearable" devices that provide various types of functionality. In other examples, hearing assistance device(s) 102 can include other types of devices that are wearable in, on, or in the vicinity of the user's ears. In other examples, hearing assistance device(s) 102 can include other types of devices that are implanted or otherwise osseointegrated with the user's skull; wherein the ear-wearable device is able to facilitate stimulation of the wearer's ears via the bone conduction pathway.

Hearing assistance devices of the present disclosure can incorporate an antenna arrangement coupled to a high-frequency radio, such as a 2.4 GHz radio. The radio can conform to an IEEE 802.11 (e.g., WIFI®) or BLUETOOTH® (e.g., BLE, BLUETOOTH® 4.2 or 5.0) specification, for example. It is understood that hearing assistance devices of the present disclosure can employ other radios, such as a 900 MHz radio. Hearing assistance devices of the present disclosure can be configured to receive streaming audio (e.g., digital audio data or files) from an electronic or digital source. Representative electronic/digital sources (also referred to herein as accessory devices) include an assistive listening system, a TV streamer, a remote microphone device, a radio, a smartphone, a cell phone/entertainment device (CPED), a remote control, or other electronic device that serves as a source of digital audio data or files.

Figure 8:
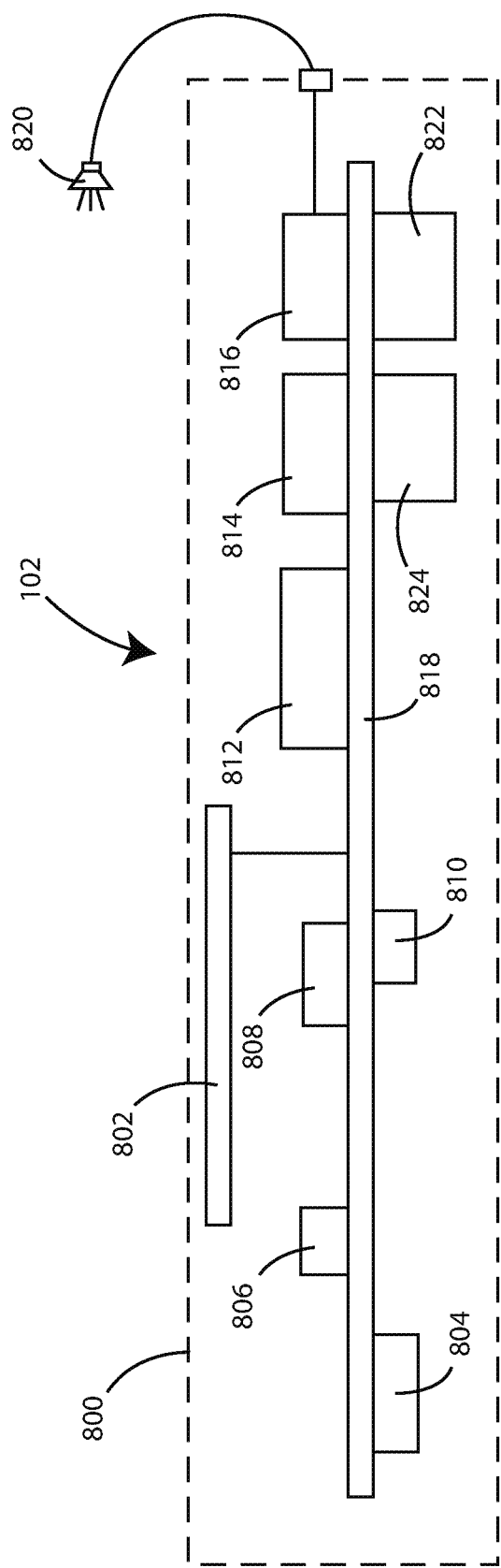
FIG. 8 is a schematic view of various components of a hearing assistance device in accordance with various embodiments herein.

Referring now to FIG. 8, a schematic block diagram is shown with various components of a hearing assistance device 102 in accordance with various embodiments. The block diagram of FIG. 8 represents a generic hearing assistance device for purposes of illustration. The hearing assistance device 102 can include several components electrically connected to a flexible mother circuit 818 (e.g., flexible mother board) which is disposed within housing 800. A power supply circuit 804 can include a battery and can be electrically connected to the flexible mother circuit 818 and provides power to the various components of the hearing assistance device 102. One or more microphones 806 are electrically connected to the flexible mother circuit 818, which provides electrical communication between the microphones 806 and a digital signal processor (DSP) 812. Among other components, the DSP 812 incorporates or is coupled to audio signal processing circuitry configured to implement various functions described herein. A sensor package 814 can be coupled to the DSP 812 via the flexible mother circuit 818. The sensor package 814 can include one or more different specific types of sensors such as those described in greater detail below. In some embodiments, one or more user switches 810 (e.g., on/off, volume, mic directional settings) are electrically coupled to the DSP 812 via the flexible mother circuit 818.

An audio output device 816 is electrically connected to the DSP 812 via the flexible mother circuit 818. In some embodiments, the audio output device 816 comprises a speaker (coupled to an amplifier). In other embodiments, the audio output device 816 comprises an amplifier coupled to an external receiver 820 adapted for positioning within an ear of a wearer. The external receiver 820 can include an electroacoustic transducer, speaker, or loud speaker. The hearing assistance device 102 may incorporate a communication device 808 coupled to the flexible mother circuit 818 and to an antenna 802 directly or indirectly via the flexible mother circuit 818. The communication device 808 can be a BLUETOOTH® transceiver, such as a BLE (BLUETOOTH® low energy) transceiver or other transceiver (e.g., an IEEE 802.11 compliant device). The communication device 808 can be configured to communicate with one or more external devices, such as those discussed previously, in accordance with various embodiments. In various embodiments, the communication device 808 can be configured to communicate with an external visual display device such as a smart phone, a video display screen, a tablet, a computer, a virtual reality display device, an augmented reality display device, or the like.

In various embodiments, the hearing assistance device 102 can also include a control circuit 822 and a memory storage device 824. The control circuit 822 can be in electrical communication with other components of the device. The control circuit 822 can execute various operations, such as those described herein. The control circuit 822 can include various components including, but not limited to, a microprocessor, a microcontroller, an FPGA (field-programmable gate array) processing device, an ASIC (application specific integrated circuit), or the like. The memory storage device 824 can include both volatile and non-volatile memory. The memory storage device 824 can include ROM, RAM, flash memory, EEPROM, SSD devices, NAND chips, and the like. The memory storage device 824 can be used to store data from sensors as described herein and/or processed data generated using data from sensors as described herein, including, but not limited to, information regarding therapy regimens, performance of the same, data regarding physiological properties, side-effects, and the like.

In various embodiments, health monitoring devices can interact with a patient to provide information and/or query or prompt the patient regarding a medication administration event, occurrence of a side effect, occurrence of a therapeutic effect, a social interaction, a nutrition event, a hydration event, an emesis event, an excretion event (e.g., a urination event, a bowel movement, etc.), or the like. In some cases, only a single health monitoring device may interact with the patient. In other cases, multiple devices may function as a system to interact with the patient.

In various embodiments, computing devices can be used as part of systems and methods herein. In some embodiments, the computing device can be a handheld computing device such as a smart phone or a tablet. The computing device can include a display screen and a camera. In some embodiments, the computing device can be a smartphone, a video monitor, a virtual reality display device, an augmented reality display device, or the like.

In some embodiments, the display screen can be a touch screen. The display screen can display various pieces of information to the patient including, but not limited to, an indication that a medication administration event has been detected, a query to the patient regarding whether a medication was just administered, an indication that a side-effect occurrence was just detected, a prompt to the patient that it is time to take a medication, or the like.

Figure 9:
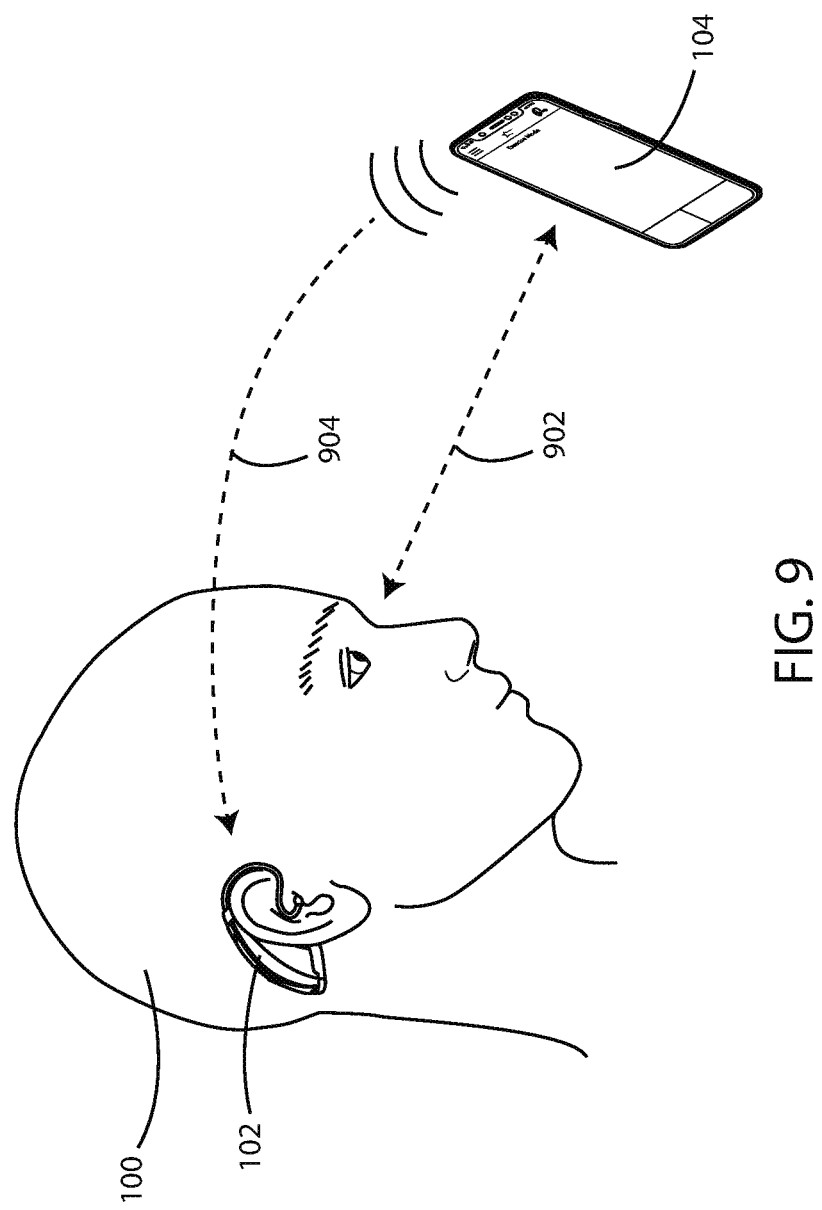
FIG. 9 is a schematic view of various components of a hearing assistance device in accordance with various embodiments herein.

Referring now to FIG. 9, a schematic view is shown of a patient 100 wearing a hearing assistance device 102 and interfacing with a handheld computing device 104. Both the hearing assistance device 102 and the handheld computing device 104 can provide audio communication 904 to the patient. The audio communication 904 can be a prompt, a piece of information, a query, an instruction, or the like. In addition, the handheld computing device 104 can provide video communication 902 to the patient.

The camera of the computing device can be positioned to face away from the display screen and back toward the patient. The camera can be used to capture an image or images of the patient's face and, in some cases, the patient's eyes. In some embodiments, the camera can be used to capture image(s) including the positioning of a patient's face, pupil, iris, and/or sclera. In some embodiments, such information can also be used to calculate angle, speed and direction of nystagmus. Aspects of nystagmus detection and characterization are described in commonly-owned U.S. Publ. Pat. Appl. No. 2018/0228404, the content of which is herein incorporated by reference.

Referring now to FIG. 10, a schematic view is shown of a handheld computing device 104 and elements of a display screen 1004 thereof in accordance with various embodiments herein. The handheld computing device 104 can include a camera 1006, a speaker 1008 and the like. Many visual display options are contemplated herein. In various embodiments, the handheld computing device 104 can display an indicator 1010 that it is time for the patient to take their medication, time to eat, time to drink, time to use the restroom, and the like. The handheld computing device 104 can also provide a prompt 1012 for the patient to take their medication. Audio prompts are also contemplated herein. Thus, the prompt 1012 can be in addition to, or instead of, an audio prompt from the hearing assistance device 102, the handheld computing device 104, or another device. The prompt(s) can be issued according to a predetermined or adaptively determined schedule. The predetermined schedule can be consistent with medications prescribed s.i.d., b.i.d., t.i.d., q.i.d., etc. For example, the predetermined schedule can once per day, every 4 hours during waking hours, every 6 hours, every 8 hours, etc.

In some embodiments, prompts (aural, visual, etc.) to eat or prepare to eat can be provided prior to or after the prompts to take a medication. In some embodiments, prompt(s) may be issued according to data analytics of the health monitoring device. In at least one embodiment, the data analytics of the health monitoring device may be used to adaptively determine which medication(s), medication strength, medication quantity, medication administration timing, and other related administration instructions to provide to the patient using a prompt. For example, if the data from the sensors is consistent with an insufficient dose or serum concentration of a medication then the schedule can be changed and/or the dose can be increased so as to increase the serum concentration of the medication. Similarly, if the data from the sensors is consistent with an overdose or too high of a serum concentration of a medication then the schedule can be changed and/or the dose can be decreased so as to decrease the serum concentration of the medication.

In some embodiments, a graphic image 1018 can be displayed to help the patient or a third party to understand the nature of the prompt. For example, the graphic image 1018 can be an image of the specific medication that the patient is supposed to take. As another example, the graphic image 1018 can be a video or animation that demonstrates an optimal medication administration method, such as a specific head movement pattern that can be readily identified by the health monitoring system and serve as a confirmation to the health monitoring system that a medication has been ingested.

In some embodiments, the handheld computing device 104 can display virtual buttons 1014, 1016 (or input icons) to accept user input from the patient through the display screen 1004. The text associated with the virtual buttons can be contextual. In some embodiments, such as when the device 104 is displaying a prompt to the patient for them to take their medication, the virtual buttons can display text so that user input from the patient regards whether they acknowledge the prompt or whether they want to delay the prompt by pushing a button, such as a virtual button labeled "snooze". However, it will be appreciated that user input/feedback can also be provided in other ways, such as by the patient speaking an answer or nodding their head.

Referring now to FIG. 11, a schematic view is shown of a handheld computing device 104 and elements of a display screen 1004 thereof in accordance with various embodiments herein. Many of the elements shown in FIG. 11 are similar to those in FIG. 10. However, in FIG. 11 the handheld computing device 104 can display an indicator 1010 that the device 104 (or another device in communication therewith) has detected a medication administration event. The handheld computing device 104 can also provide a query 1112 for the patient to confirm whether they have taken their medication. In this example, the handheld computing device 104 can display virtual buttons 1014, 1016 (or input icons) to accept patient input regarding whether they have taken their medication. In this manner, detection of a medication administration event can be validated/adjudicated. By tracking this information over time, detection can be made more accurate. In specific, a supervised machine-learning approach can be applied to make the detection algorithm more accurate over time.

Sensors

Hearing assistance devices herein can include one or more sensor packages to provide data to determine various aspects including, but not limited to, detect the occurrence or presence of side-effects, detect compliance/non-compliance with a therapeutic regimen, detect the occurrence or presence of medication administration events and signs of fall risk alert, detect social interactions, detect nutritional events, detect urination events, and the like.

The sensor package can comprise one or a multiplicity of sensors. In some embodiments, the sensor packages can include one or more motion sensors amongst other types of sensors. Motion sensors herein can include inertial measurement units (IMU), accelerometers, gyroscopes, barometers, altimeters, and the like. Motions sensors can be used to track movement of a patient in accordance with various embodiments herein.

In some embodiments, the motion sensors can be disposed in a fixed position with respect to the head of a patient, such as worn on or near the head or ears. In some embodiments, the motion sensors can be worn on or near another part of the body such as on a wrist, arm, or leg of the patient.

According to various embodiments, the sensor package can include one or more of an IMU, and accelerometer (3, 6, or 9 axis), a gyroscope, a barometer, an altimeter, a magnetometer, a magnetic sensor, an eye movement sensor, a pressure sensor, an acoustic sensor, a telecoil, a heart rate sensor, a global positioning system (GPS), a temperature sensor, a blood pressure sensor, an oxygen saturation sensor, an optical sensor, a blood glucose sensor (optical or otherwise), a galvanic skin response sensor, a cortisol level sensor (optical or otherwise), a microphone, acoustic sensor, an electrocardiogram (ECG) sensor, electroencephalography (EEG) sensor which can be a neurological sensor, eye movement sensor (e.g., electrooculogram (EOG) sensor), myographic potential electrode sensor (EMG), a heart rate monitor, a pulse oximeter, a wireless radio antenna, blood perfusion sensor, hydrometer, sweat sensor, cerumen sensor, air quality sensor, pupillometry sensor, cortisol level sensor, hematocrit sensor, light sensor, image sensor, and the like.

In some embodiments, the sensor package can be part of a hearing assistance device. However, in some embodiments, the sensor packages can include one or more additional sensors that are external to an assistive listening device. For example, various of the sensors described above can be part of a wrist-worn or ankle-worn sensor package, or a sensor package supported by a chest strap.

Data produced by the sensor(s) of the sensor package can be operated on by a processor of the device or system.

As used herein the term "inertial measurement unit" or "IMU" shall refer to an electronic device that can generate signals related to a body's specific force and/or angular rate. IMUs herein can include one or more accelerometers (3, 6, or 9 axis) to detect linear acceleration and a gyroscope to detect rotational rate. In some embodiments, an IMU can also include a magnetometer to detect a magnetic field.

The eye movement sensor may be, for example, an electrooculographic (EOG) sensor, such as an EOG sensor disclosed in commonly owned U.S. Pat. No. 9,167,356, which is incorporated herein by reference. The pressure sensor can be, for example, a MEMS-based pressure sensor, a piezo-resistive pressure sensor, a flexion sensor, a strain sensor, a diaphragm-type sensor and the like.

The temperature sensor can be, for example, a thermistor (thermally sensitive resistor), a resistance temperature detector, a thermocouple, a semiconductor-based sensor, an infrared sensor, or the like.

The blood pressure sensor can be, for example, a pressure sensor. The heart rate sensor can be, for example, an electrical signal sensor, an acoustic sensor, a pressure sensor, an infrared sensor, an optical sensor, or the like.

The oxygen saturation sensor (such as a blood oximetry sensor) can be, for example, an optical sensor, an infrared sensor, or the like.

The electrical signal sensor can include two or more electrodes and can include circuitry to sense and record electrical signals including sensed electrical potentials and the magnitude thereof (according to Ohm's law where V=IR) as well as measure impedance from an applied electrical potential.

It will be appreciated that the sensor package can include one or more sensors that are external to the hearing assistance device. In addition to the external sensors discussed hereinabove, the sensor package can comprise a network of body sensors (such as those listed above) that sense movement of a multiplicity of body parts (e.g., arms, legs, torso). In some embodiments, the hearing assistance device can be in electronic communication with the sensors or processor of another medical device, e.g., an insulin pump device or a heart pacemaker device.

Medication Administration Detection

In various embodiments herein, the system can evaluate signals from various sensors to detect a medication administration event (or therapy administration event). By way of example, data from a movement sensor can be used to detect a medication administration event. Movement data indicating tipping of the head backward by at least a threshold amount can be used to detect a medication administration event. By way of example, data from a microphone can be used to detect a medication administration event. Sound data consistent with a swallowing action on the part of the patient can be used to detect a medication administration event.

In some embodiments, data from a movement sensor indicative of the head tipping backward in combination with data from a microphone indicative of swallowing can be used to detect a medication administration event. In some embodiments, the health monitoring device can be configured to evaluate a signal from at least one of the sensors of the sensor package to detect at least one of chewing and swallowing. In some embodiments, the health monitoring device can be configured to evaluate a signal from at least one of the sensors of the sensor package to detect swallowing of a liquid.

In some embodiments, the health monitoring device can be configured to query the hearing assistance device wearer to confirm an instance of a detected medication administration event.

In some embodiments, the health monitoring device can be configured to accept input from the hearing assistance device wearer regarding confirmation of an instance of a detected medication administration event. The input can take various forms. In some embodiments, the input can include at least one of a head gesture input and a spoken input.

The system can apply various machine learning techniques to the various sensor data inputs to determine a probability that a medication administration event occurred. As previously described, the machine learning techniques can be improved, over time, through application of supervised learning techniques, such as prompting the user to indicate whether or not they had actually taken a medication when a detected medication administration event occurred.

It is understood that therapeutic/medication administration regimens herein can be wholistic and can encompass recommendations for physical activities, changes in diet, etc.

In some embodiments, the system can receive data indicating that administration of a therapy has taken place. For example, the system can receive an input from the patient or a care provider that administration of a therapy has taken place. As another example, the system can receive an input from another system or device that administration of a therapy has taken place. In some embodiments, an input can be received from a system related to dispensing, administration, or disbursement. For example, an input can be received from a POS (point-of-sale) system, or an automated medication dispenser. As another example, the system can receive an input from a smart pill bottle or another device indicating that administration of a therapy has taken place. As still another example, the system can detect that administration of a therapy has taken place by detecting the effects of administration of a therapy, such as by evaluating sensor data to detect the effects of administration of a therapy. In some embodiments, detected effects can be short-term effects/changes. For example, a change in gait or a change in detected patterns of motion that occur over time spans of seconds, minutes, or hours. In some embodiments, detected effects can be long-term effects/changes. In some embodiments, detected effects can be transitory effects/changes (such as may result from a one-time administration of a therapy). In some embodiments, detected effects can be chronic effects/changes.

Side-Effect and Therapeutic Effect Detection

In various embodiments herein, the health monitoring device can be configured to evaluate signals from one or more sensors, and/or signals from separate devices, and/or patient input to detect an adverse medication side effect. Various side effects can be detected including, but not limited to, orthostatic hypotension, increased postural sway, unsteadiness, impaired alertness, dizziness, dry mouth, changes in mood or behavior, seizure, depression, insomnia, difficulty thinking, fever, abnormal heart rhythms, nausea, abnormal bowl movements, difficulty swallowing, and loss of appetite. Similarly, in various embodiments herein, the health monitoring device can be configured to evaluate signals from one or more sensors, and/or signals from separate devices, and/or patient input to detect a therapeutic effect and/or the absence of side effects.

In various embodiments, the hearing assistance device can be configured to evaluate a signal from at least one of the sensors of the sensor package to detect one or more of a vestibular disturbance and nystagmus. In various embodiments, the system can detect emesis of the patient. Emesis can be detected based on characteristic acoustic patterns and/or characteristic postural and diaphragm/abdominal contraction patterns. In various embodiments, emesis can be detected by analyzing signals from at least one of an IMU and a microphone.

In some embodiments, the system can receive information regarding the side effect directly from the patient, such as though patient input through a display screen or audible patient input. In some embodiments, the system can display a confirmation query to the patient after side effects have been detected.

In some embodiments, the health monitoring device can be configured to evaluate a signal from at least one of the sensors of the sensor package to detect a change in average daily physical activity or social engagement, which could be indicative of a side-effect or a therapeutic effect depending on whether the change is negative or positive. Various techniques for measuring social engagement, physical activity, levels and other aspects of the user's physical and mental wellness may be applied, such as those described in U.S. patent application Ser. No. 16/777,494 ("Efficient Wellness Measurement in Ear-Wearable Devices") and Ser. No. 16/777,525 ("Detection of Physical Abuse or Neglect Using Data From Ear-Wearable Devices"), the content of which is herein incorporated by reference. In some embodiments, the health monitoring system can detect decreases in physical activity, worsening of mood or depression, fewer social encounters, decreased social engagement complexity, and the like as a side effect of one or more medications. In some embodiments, the health monitoring system can be configured to detect improvements in symptoms after beginning a new medication or switching medication regiments.

In various embodiments, the health monitoring device can be configured to evaluate a signal from at least one of the sensors of the sensor package to detect a change in mood or signs of depression.

Notifications regarding detected side effects can be handled in various ways. In some embodiments, a notification of the detected side effect is sent to an external device. In some embodiments, a notification of the detected side effect is sent to an electronic medical record system. In some embodiments, a notification of the detected side effect is sent to a pharmacist, physician, therapist, or the like. In some embodiments, a notification of the detected side effect is sent to an electronic medical record system. In some embodiments, a notification of the detected side effect is sent to a pharmacist through a pharmacy management system. In some embodiments, a notification of the detected side effect is sent to an insurer or payor system.

Excretion Event Detection

In various embodiments herein, the system can evaluate signals from various sensors to detect an excretion event. In some contexts, an excretion event, such as a urination event, results in a characteristic sound pattern that can be recorded by a microphone associated with the health monitoring device. By way of example, the control circuit can be configured to evaluate a signal from at least one of the motion sensor and the microphone to detect an excretion event. In various embodiments, the excretion event can then be recorded along with a timestamp. In various embodiments, the control circuit is further configured to further evaluate a signal from a location sensor to detect an excretion event and record the event along with a timestamp. In such a scenario, the combination of data from the location sensor and the microphone can be used to detect an excretion event. For example, if the data from the location sensor indicates that the patient has moved into a bathroom, then this information along with data from the microphone can be used to detect a likely excretion event. In a similar manner, other excretion and excretion-related events can also be detected beyond urination including, but not limited to, bowel movements, constipation, diarrhea and the like.

In some embodiments, the system can prompt the patient to provide input into the device regarding a urination or other excretory event such that the system can then match recorded data against the event and then identify a future event when the same data pattern is observed. In some embodiments, the system can receive a signal from a separate device (basin, toilet, etc.) that an event has occurred. In some embodiments, the system can receive information regarding the event directly from the patient, such as though patient input through a display screen or audible patient input. In some embodiments, the system can display a confirmation query to the patient after a likely event has been detected.

In some embodiments, the system can estimate one or more of urine volume and urine flow rate based on the microphone data. In various embodiments, the control circuit uses calibration data (e.g., a calibration curve) to convert sensor data into urine flow data.

As described above, the system can identify occurrences of swallowing of liquids. Thus, in various embodiments, the system and/or control circuit can be further configured to estimate fluid balance changes based on detected urination and detecting swallowing of liquids.

Notifications regarding a detected urination or other event can be handled in various ways. In some embodiments, a notification of the urination or other event is sent to an external device. In some embodiments, a notification of the urination or other event is sent to an electronic medical record system. In some embodiments, a notification of the urination or other event is sent to a pharmacist. In some embodiments, a notification of the urination or other event is sent to an electronic medical record system. In some embodiments, a notification of the urination or other event is sent to a pharmacist through a pharmacy management system.

Detection of Predisposition for Falls

In some embodiments, the health monitoring system is adapted to detect changes in the patient's predisposition for falling. Exemplary fall risk assessment or fall risk prediction methods are described in U.S. Publ. Pat. App. No. 2018/0228404, titled "Fall prediction system and method of using same", the content of which is herein incorporated by reference in its entirety. For example, a fall prediction system can include a hearing device for a wearer, a sensor operatively connected to the hearing device and adapted to detect a characteristic of the wearer and generate a sensor signal based on the characteristic, wherein the characteristic includes at least one of a physiological characteristic and an environmental characteristic of the wearer, and a controller operatively connected to the hearing device. The controller can be adapted to determine a fall risk value based on the sensor signal, compare the fall risk value to a fall risk threshold, and generate a fall prevention output if the fall risk value exceeds the fall risk threshold. In at least one embodiment, a fall prevention output may be a notification to a pharmacist or an entry into an electronic health record system. For example, the health monitoring device may be operatively connected to a pharmacy management system such that, when a prescription is to be filled for the patient, the pharmacist will be automatically alerted, by the pharmacy management system's Consultation Application (CAP), to the patient's determined fall risk level. In some embodiments, the pharmacist may be alerted to the patient's fall risk level during the patient's drug utilization review (DUR).

Methods

Many different methods are contemplated herein, including, but not limited to, methods of making, methods of using, and the like. Aspects of system/device operation described elsewhere herein can be performed as operations of one or more methods in accordance with various embodiments herein.

In an embodiment, a method of operating a health monitoring device is included, the method placing the health monitoring device in the presence of a patient, the health monitoring device can include; a control circuit; a electroacoustic transducer for generating sound in electrical communication with the control circuit; a power supply circuit in electrical communication with the control circuit; and a sensor package in electrical communication with the control circuit; processing the signal from at least one of the sensors of the sensor package to detect administration of a therapy to the patient; and recording an instance of a detected medication administration event along with a timestamp.

In an embodiment of the method, the sensor package can include at least one, two, three, four, five, six, seven, eight, nine or ten of the sensors described above.

In an embodiment, the method can further include issuing a prompt (aural and/or haptic and/or visual) to a hearing assistance device wearer to administer a therapy, time for the patient to take their medication, time to eat, time to drink, time to use the restroom, etc. In an embodiment of the method, the prompt can be issued according to a predetermined schedule or an adaptively determined schedule. The predetermined schedule can be consistent with medications prescribed s.i.d., b.i.d., t.i.d., q.i.d., etc. For example, the predetermined schedule can once per day, every 4 hours during waking hours, every 6 hours, every 8 hours, etc.

In an embodiment, the method can further include sending a notification of the instance of the detected medication administration event to an external device. In an embodiment, the method can further include sending a notification of the instance of the detected medication administration event to an electronic medical record system. In an embodiment, the method can further include sending a notification of the instance of the detected medication administration event to a pharmacist through a pharmacy management system.

In an embodiment, the method can further include sending data can include a plurality of detected instances of medication administration events to an electronic medical record system. In an embodiment, the method can further include sending data can include a plurality of detected instances of medication administration events, occurrences of side effects, social interactions, nutrition events, hydration events, emesis events, excretion events, and the like to a pharmacist through a pharmacy management system.

In an embodiment, the method can further include evaluating a signal from at least one of the sensors of the sensor package to detect at least one of chewing and swallowing. In an embodiment, the method can further include evaluating a signal from at least one of the sensors of the sensor package to detect swallowing of a liquid and/or eating of food. In an embodiment, the method can further include evaluating a signal from a smart water bottle, a smart cup, a smart plate, or other nutrition monitoring system to detect swallowing of a liquid and/or eating of food.

In an embodiment, the method can further include querying the hearing assistance device wearer to confirm an instance of a detected medication administration event. In an embodiment, the method can further include accepting an input from the hearing assistance device wearer regarding confirmation of an instance of a detected medication administration event. In an embodiment of the method, the input comprises at least one of a head gesture input, a spoken input, and a button-press input.

In an embodiment, the method can further include evaluating a signal from at least one of the sensors of the sensor package to detect an adverse medication side effect. In an embodiment, the adverse medication side effect can include at least one of orthostatic hypotension, increased postural sway, unsteadiness, impaired alertness, dizziness, dry mouth, changes in mood or behavior, seizure, depression, insomnia, difficulty thinking, fever, abnormal heart rhythms, nausea, abnormal bowel movements, difficulty swallowing, and loss of appetite. In an embodiment, the method can further include evaluating a signal from at least one of the sensors of the sensor package to detect one or more of a vestibular disturbance and nystagmus. In an embodiment, the method can further include evaluating a signal from at least one of the sensors of the sensor package to detect a change in average daily physical activity or social activity. In an embodiment, the method can further include evaluating a signal from at least one of the sensors of the sensor package to detect a change in mood or signs of depression.

In an embodiment, a method of operating a health monitoring device is included, the method placing the health monitoring device in the presence of a patient, the health monitoring device can include; a control circuit; a motion sensor in electrical communication with the control circuit; a microphone in electrical communication with the control circuit; an electroacoustic transducer for generating sound in electrical communication with the control circuit; a power supply circuit in electrical communication with the control circuit; evaluating a signal from at least one of the motion sensor and the microphone to detect an excretion or excretion-related event; and recording an instance of a detected urination event along with a timestamp.

In an embodiment, the method can further include evaluating a signal from a location sensor to detect a urination event and record the urination event along with a timestamp. In an embodiment, the method can further include evaluating a signal from at least one of the motion sensor and the microphone to detect swallowing of liquids and recording the same along with a timestamp.

In an embodiment, the method can further include estimating fluid balance changes based on detected urination and detecting swallowing of liquids. In an embodiment of the method, the control circuit uses calibration data to convert sensor data into urine flow data. In an embodiment of the method, the control circuit receives data from a separate device, the data including urine volume data.

In an embodiment, the method can further include sending a notification of the urination event to an external device.

In an embodiment, the method can further include sending a notification of the urination event to an electronic medical record system. In an embodiment, the method can further include sending a notification of the urination event to a pharmacist. In an embodiment, the method can further include sending a notification of the urination event to an electronic medical record system. In an embodiment, the method can further include sending a notification of the urination event to a pharmacist through a pharmacy management system.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. An ear-wearable hearing assistance device comprising a control circuit;
an electroacoustic transducer for generating sound in electrical communication with the control circuit;
a power supply circuit in electrical communication with the control circuit;
a sensor package disposed within the hearing assistance device and in electrical communication with the control circuit, the sensor package comprising a movement sensor;

wherein the control circuit is configured to evaluate a signal from at least one of the sensors of the sensor package to detect administration of a therapy, wherein the administration of a therapy comprises a medication administration event, and wherein the control circuit is configured to evaluate movement data from the movement sensor indicating tipping of a head backward by at least a threshold amount to initially detect the medication administration event; and wherein the control circuit is configured to record an instance of a therapy administration event along with a timestamp.

2. The hearing assistance device of claim 1, the sensor package comprising at least two of a motion sensor, an IMU, an accelerometer (3, 6, or 9 axis), a gyroscope, a barometer, an altimeter, a magnetometer, a magnetic sensor, an eye movement sensor, a pressure sensor, an acoustic sensor, a telecoil, a heart rate sensor, a global positioning system (GPS) sensor, a temperature sensor, a blood pressure sensor, a pulse oximeter sensor, an optical sensor, a light sensor, a blood glucose sensor, a galvanic skin response sensor, a cortisol level sensor, a microphone, acoustic sensor, an electrocardiogram (ECG) sensor, an electroencephalography (EEG) sensor, sensor, an electrooculogram (EOG) sensor, a myographic potential electrode sensor (EMG), a blood perfusion sensor, hydrometer, a sweat sensor, a cerumen sensor, an air quality sensor, a pupillometry sensor, a cortisol level sensor, a hematocrit sensor, and an image sensor.

3. The hearing assistance device of claim 1, the control circuit further configured to issue a prompt to a hearing assistance device wearer to administer a therapy.

4. The hearing assistance device of claim 1, wherein the control circuit is configured to send a notification of the instance of the detected therapy administration event to an electronic medical record system.

5. The hearing assistance device of claim 1, wherein the control circuit is configured to send a notification of the instance of the detected therapy administration event to a pharmacist through a pharmacy management system.

6. The hearing assistance device of claim 1, wherein the control circuit is configured to evaluate a signal from at least one of the sensors of the sensor package to detect at least one of chewing and swallowing.

7. The hearing assistance device of claim 1, wherein the control circuit is configured to evaluate a signal from at least one of the sensors of the sensor package to detect swallowing of a liquid.

8. The hearing assistance device of claim 1, the control circuit is configured to query the hearing assistance device wearer to confirm an instance of a detected therapy administration event.

9. The hearing assistance device of claim 1, wherein the control circuit is configured to evaluate a signal from at least one of the sensors of the sensor package to detect an adverse medication side effect.

10. The hearing assistance device of claim 9, the adverse medication side effect comprising at least one of orthostatic hypotension, increased postural sway, unsteadiness, impaired alertness, dizziness, dry mouth, changes in mood or behavior, seizure, depression, insomnia, difficulty thinking, fever, abnormal heart rhythms, nausea, abnormal bowel movements, difficulty swallowing, and loss of appetite.

11. The hearing assistance device of claim 1, wherein the control circuit is configured to evaluate a signal from at least one of the sensors of the sensor package to detect a change in average daily physical activity.

12. The hearing assistance device of claim 1, wherein the control circuit is configured to evaluate a signal from at least one of the sensors of the sensor package to detect one or more of a vestibular disturbance and nystagmus.

13. The hearing assistance device of claim 1, the sensor package further comprising a light sensor.

14. The hearing assistance device of claim 1, wherein the control circuit is configured to evaluate sensor data from at least one sensor of the sensor package to detect therapeutic or side-effects of the medication administration event.

15. The hearing assistance device of claim 1, wherein the control circuit is configured to evaluate sensor data from at least one sensor of the sensor package to detect a change in average daily physical activity or social engagement.

16. The hearing assistance device of claim 1, wherein the control circuit is configured to confirm an instance of a detected therapy administration event by evaluating a signal from at least one of the sensors of the sensor package to detect a change in physiological data correlated with the medication administration event.

* * * * *